(12) United States Patent
Faccioli et al.

(10) Patent No.: US 9,247,979 B2
(45) Date of Patent: Feb. 2, 2016

(54) DEVICE TO PREPARE AND ADMINISTER A TWO-COMPONENT MIXTURE

(75) Inventors: Giovanni Faccioli, Monzambano (IT); Renzo Soffiatti, Nogara (IT)

(73) Assignee: TECRES S.P.A., Sommacampagna (Verona) (IT)

( * ) Notice: Subject to any disclaimer, the term of this patent is extended or adjusted under 35 U.S.C. 154(b) by 685 days.

(21) Appl. No.: 13/122,129

(22) PCT Filed: Jan. 25, 2010

(86) PCT No.: PCT/IB2010/050320
§ 371 (c)(1),
(2), (4) Date: Mar. 31, 2011

(87) PCT Pub. No.: WO2011/089480
PCT Pub. Date: Jul. 28, 2011

(65) Prior Publication Data
US 2012/0155214 A1    Jun. 21, 2012

(51) Int. Cl.
| | | |
|---|---|---|
| B01F 13/00 | (2006.01) | |
| A61B 17/88 | (2006.01) | |
| B01F 11/00 | (2006.01) | |
| B01F 15/00 | (2006.01) | |
| B01F 15/02 | (2006.01) | |

(52) U.S. Cl.
CPC ......... *A61B 17/8825* (2013.01); *A61B 17/8827* (2013.01); *B01F 11/0054* (2013.01); *B01F 13/0023* (2013.01); *B01F 15/00506* (2013.01); *B01F 15/0206* (2013.01); *B01F 15/0279* (2013.01); *A61B 2017/8838* (2013.01)

(58) Field of Classification Search
CPC ............... B01F 13/002; B01F 15/0205; B01F 2215/0029; B01F 15/0206; B01F 15/00506
USPC ............. 366/139, 130; 206/137, 222; 604/82, 604/87, 88, 89
See application file for complete search history.

(56) References Cited

U.S. PATENT DOCUMENTS

| | | | | |
|---|---|---|---|---|
| 5,193,907 | A  * | 3/1993  | Faccioli et al. | 366/130 |
| 6,406,175 | B1 * | 6/2002  | Marino | 366/130 |
| 6,736,537 | B2 * | 5/2004  | Coffeen et al. | 366/130 |
| 7,018,089 | B2 * | 3/2006  | Wenz et al. | 366/130 |
| 8,690,419 | B2 * | 4/2014  | Faccioli et al. | 366/139 |
| 2005/0270897 | A1 * | 12/2005 | McCoy | 366/130 |
| 2006/0164913 | A1 * | 7/2006  | Arramon | 366/139 |
| 2007/0016128 | A1 * | 1/2007  | Keller | 604/89 |
| 2011/0004156 | A1 * | 1/2011  | Keller | 604/82 |

(Continued)

FOREIGN PATENT DOCUMENTS

| | | | | |
|---|---|---|---|---|
| WO | WO2006123205 | A1 * | 11/2006 | A61F 2/46 |
| WO | WO 2009105905 | A1 * | 9/2009 | B01F 13/00 |

*Primary Examiner* — Joseph S Del Sole
*Assistant Examiner* — Nahida Sultana
(74) *Attorney, Agent, or Firm* — Tutunjian & Bitetto, P.C.

(57) ABSTRACT

A device to prepare and administer a two-component mixture, including a first chamber in which a container is housed that is hermetically closed for a liquid component, a second chamber containing a powdered component, an opening of the container of the liquid component, a mixing member placed in the second chamber for preparing the mixture and a piston able to move in the second chamber to dispense the mixture. The mixing member includes a stem, passing through an opening for dispensing the mixture in the second chamber, having an outer end equipped with a handle and an inner end provided with a mixing blade connected to the inner end with a releasable connection.

22 Claims, 5 Drawing Sheets

(56) References Cited

U.S. PATENT DOCUMENTS

| | | | |
|---|---|---|---|
| 2011/0176382 A1* | 7/2011 | Collins | 366/130 |
| 2012/0026823 A1* | 2/2012 | Greter | B01F 3/10 366/130 |
| 2012/0116301 A1* | 5/2012 | Faccioli | A61B 17/8822 604/92 |
| 2012/0206992 A1* | 8/2012 | Stewart | 366/130 |
| 2013/0035664 A1* | 2/2013 | Mojdehbakhsh | A61M 5/284 604/506 |
| 2013/0090596 A1* | 4/2013 | Asai | A61M 5/284 604/89 |
| 2013/0237905 A1* | 9/2013 | Holmqvist | A61M 5/31525 604/89 |
| 2013/0345626 A1* | 12/2013 | Tennican | A61M 5/008 604/89 |
| 2014/0058320 A1* | 2/2014 | Hansen | A61M 5/2448 604/89 |
| 2015/0157804 A1* | 6/2015 | Baba | A61M 5/31596 604/89 |
| 2015/0190584 A1* | 7/2015 | Bar-Shalom | A61M 5/31596 604/89 |

* cited by examiner

DEVICE TO PREPARE AND ADMINISTER A TWO-COMPONENT MIXTURE

RELATED APPLICATION INFORMATION

This application claims priority to International Application No. PCT/IB2010/050320 filed on Jan. 25, 2010 the entirety of which is incorporated herein by reference.

TECHNICAL FIELD OF THE INVENTION

The present invention concerns a device to prepare and administer a two-component mixture.

More specifically, the present invention concerns a device for preparing and administering a bone cement consisting of two components, one of which is liquid and the other is powdered.

BACKGROUND

Devices for preparing and administering bone cement are known that comprise two separate chambers in which the two components that make up the bone cement are stored, said components typically being a liquid component and a powdered component. As known, in order to obtain an effective application of the bone cement during surgery, such two components must be mixed on the spot, i.e. in the operating room when the operation is being carried out.

In some known devices the liquid component is enclosed in a hermetically closed container, like for example a glass vial, so as to maintain the sterility of the component itself and to avoid it being lost into the atmosphere, since it is particularly toxic to people in the operating room. The aforementioned container is usually housed in one of the two chambers of the device and is opened or broken at the moment of use, so that the liquid itself then flows, in a spontaneous or forced marmer, into the chamber in which the powdered component is stored to mix with it.

The bone cement thus obtained is dispensed through a mobile piston inside the mixing chamber, through a suitable opening.

In known devices the mixing of the two components, after they have been brought into contact with each other in the way described, can take place by manual shaking by the operator, or else by using a special mixing member, which acts inside the chamber in which the two components are located.

In order to make it easier to mix the two components, in some known devices the mixing member is positioned coaxial to the dispensing piston and on the opposite side with respect to it:

this arrangement of the components allows the device to be held securely and comfortably during the actuation of the mixing member.

At the same time, such an arrangement of components, for reasons of practicality, simplicity and cost-effectiveness of production, requires the dispensing of the mixture to occur from the same opening through which the mixing member passes and is actuated.

In some known devices, at the end of the device with which the mixing member is associated, there is a cap to which the member itself is connected. At the end of the preparation of the mixture, it is necessary to remove the cap together with the mixing member in order to be able to dispense the preparation thrusted by the piston. This last operation, as well as being cumbersome and not very practical during surgery in an operating room, is not without drawbacks.

Firstly, indeed, there is a high probability of the preparation, when exposed to the air, contaminating, becoming unsuitable for application.

Secondly, it can accidentally come out from the device placing the health of the people present in the room at risk due to its high toxicity, and requiring a series of other provisions and safety measures to protect these people.

SUMMARY OF THE INVENTION

The technical task of the present invention is therefore to improve the state of the art.

In such a technical task, a purpose of the present invention is to provide a device for preparing and administering a mixture of two components that is practical and safe to use both during the preparation of the mixture and when the preparation is being dispensed.

Yet another purpose of the present invention is to provide a device for preparing and administering a mixture of two components without risk of contamination and/or leaking of the mixture while it is being dispensed.

A further purpose of the present invention is to make a device to prepare and administer a two-component mixture that allows the application of the mixture to be simplified and made more cost-effective, mainly but not exclusively in terms of the measures for protecting personnel.

These and other purposes are all accomplished by the device to prepare and administer a two-component mixture according to one or more of the attached claims.

An important advantage achieved by the device according to the present invention consists of the fact that the dispensing of the mixture takes place without risk of contamination of the preparation by contact with the outside.

Another advantage achieved by the device according to the present invention consists of the fact that the risks of dispersion of the prepared mixture into the outside environment are eliminated.

Yet another advantage achieved by the device according to the present invention consists of the fact that, once the preparation of the mixture has ended, the dispensing thereof during surgery can be performed with a quick and simple manual operation, which does not require further equipment or particularly complex safety measures.

A further advantage achieved by the device according to the present invention consists of the fact that the preparation of the mixture of the liquid component and of the solid component can be carried out in a practical and safe manner that is comfortable for the operator.

BRIEF DESCRIPTION OF THE DRAWINGS

These and further advantages will be more clearly understood by any man skilled in the art from the following description and from the attached drawings, given as non-limiting examples, in which.

DETAILED DESCRIPTION OF THE PREFERRED EMBODIMENTS

Figures 1, 2:
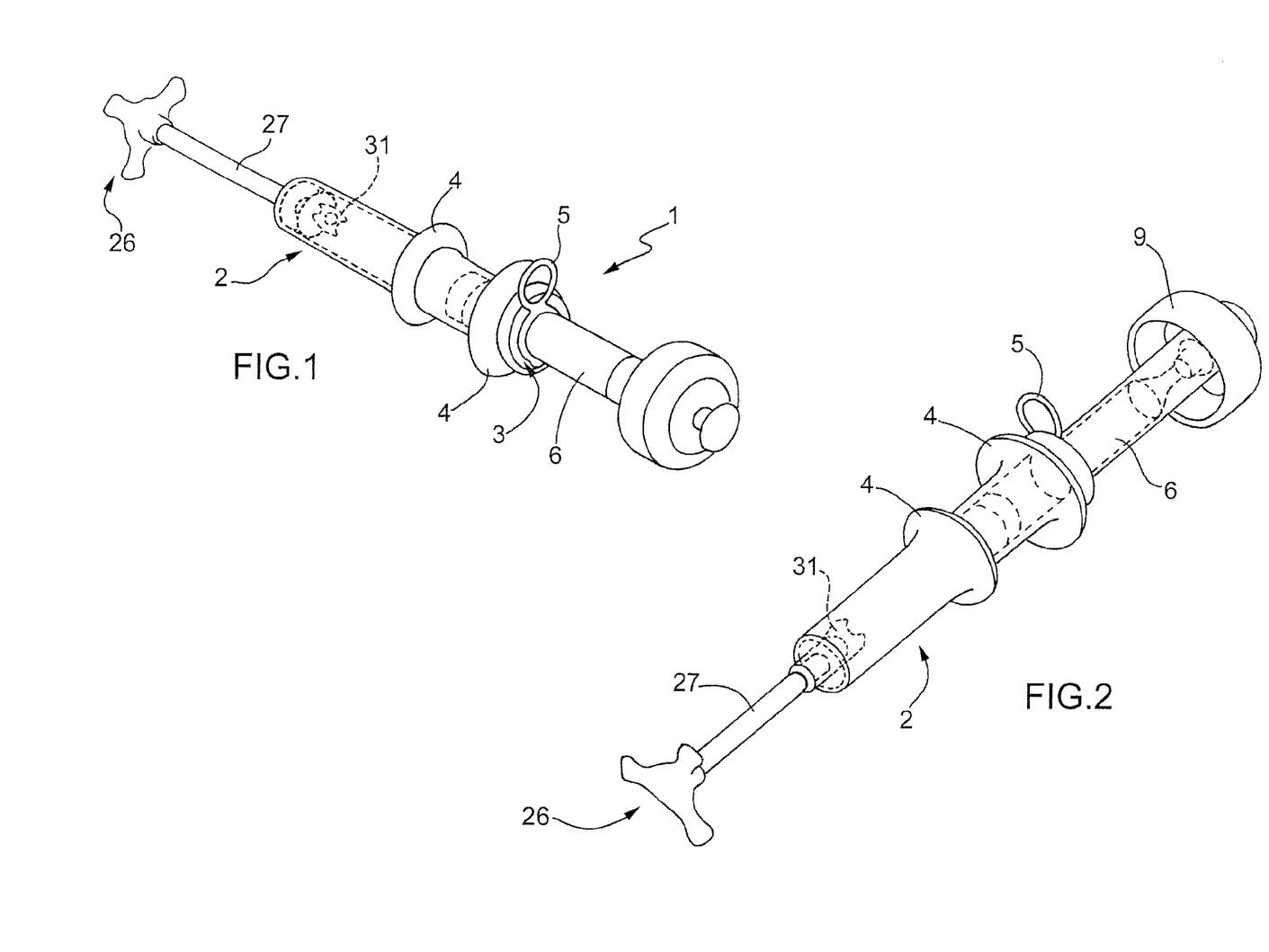
FIG. 1 is a perspective view of the device according to the invention.
FIG. 2 us a further perspective view of the device according to the, invention.
Figure 3:
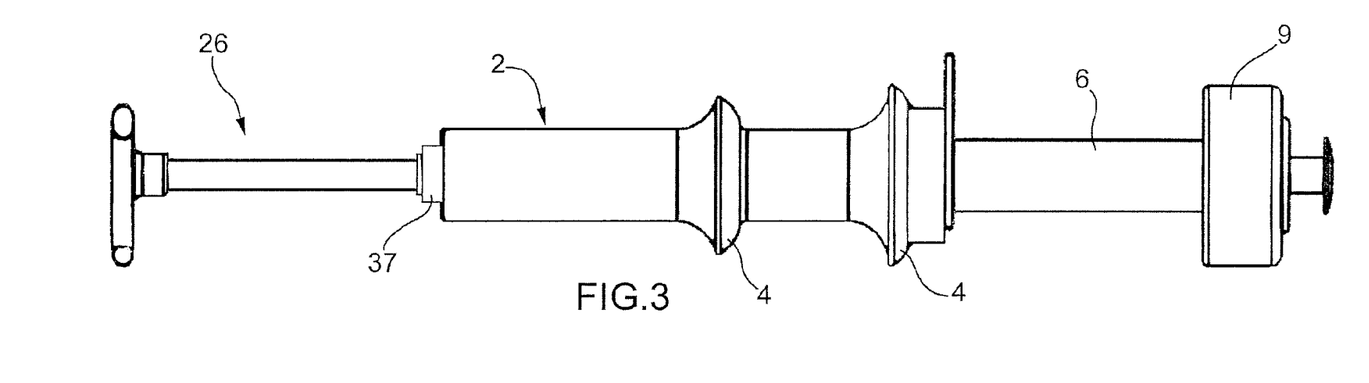
FIG. 3 is a side view of the device.

With reference to the representation of FIG. 1, a device for preparing and administering a mixture of two components according to the invention is wholly indicated with 1.

The device is particularly, but not exclusively, recommended for preparing a mixture consisting of bone cement, deriving from the union of a liquid component and a solid component, to be administered to the patient in certain types of surgery, for example osteoplastic surgery or similar. In order to obtain a suitable product, such preparation takes place, as known, in an operating room while the surgery itself is being performed.

The device 1 comprises a tubular body, wholly indicated with 2, with a substantially cylindrical configuration; at one of the bases the tubular body 2 is open, and defines a circular mouth 3.

The tubular body 2, at the mouth 3 and at the mid-way point, has two collars 4 that are joined and ergonomically configured that allow it to be held more easily during the preparation of the mixture; moreover, the tubular body 2 is equipped with an outer ring that can be used both to make it easier to hold and to connect or fix the device onto other machines or equipment.

The tubular body 2 can, for example, be made from plastic material, or else from any other material—for example metal or glass—that is suitable for containing the two components that will constitute the mixture.

The mouth 3 of the tubular body 2 has a piston 6 engaged in it, which has the function of dispensing the prepared mixture, as will become clearer hereafter.

The piston 6 is engaged in the mouth 3 so as to be able to slide axially; the piston 6 is equipped with a head 7 carrying a first sealing gasket 8 along the inner surface of the tubular body 2. Alternatively, the piston can be coupled with the tubular body 2 through a screw-nut screw connection, allowing the operator to act with greater ease considering the high density and viscosity of the mixture produced. At the opposite end with respect to the head 7, the piston 6 is provided with a substantially discoidal handle 9 that allows it to be actuated, as described hereafter.

Figure 4:
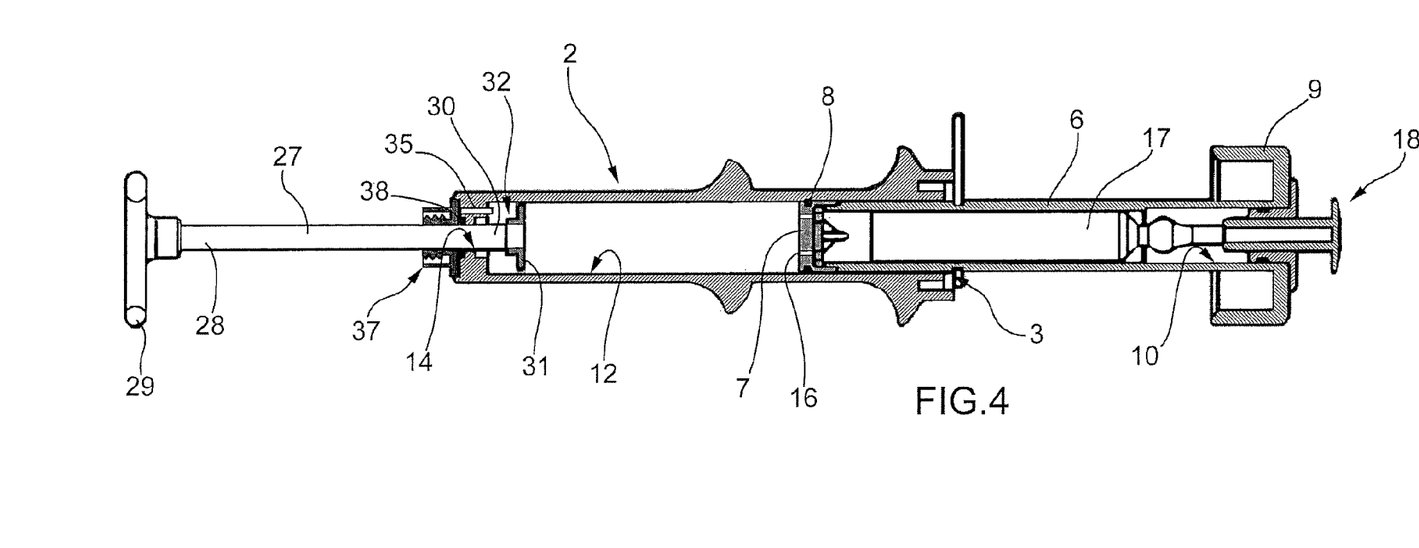
FIG. 4 is a section view of the device.

As can be seen, for example, in FIG. 4 and thereafter, the piston 6 is made internally hollow: the cavity of the piston 6 constitutes a first chamber 10 for the liquid component 11 that will constitute the mixture.

The tubular body 2, on the other hand, defines a second chamber 12 inside it, in which the powdered component 13 that has to be combined with the liquid component 11 coming from the first chamber 10 is contained. The second chamber 12 is closed by the head 7 of the piston 6.

Figure 7:
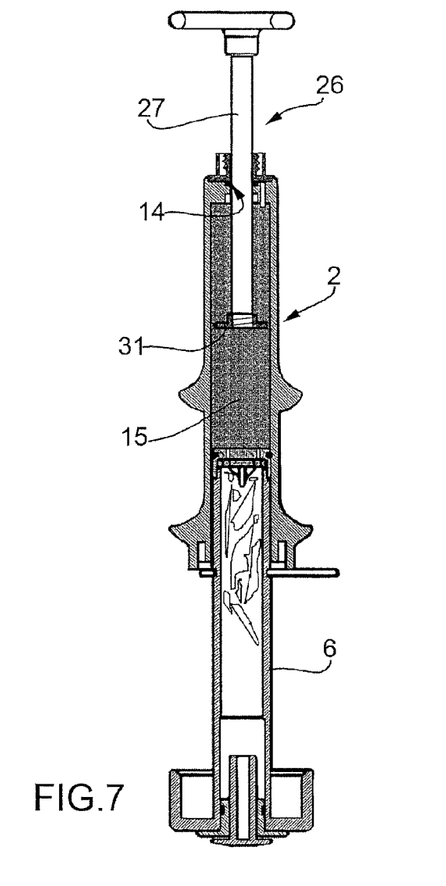
FIG. 7 is a section view of the device in another step of the preparation of the mixture.
Figure 8:
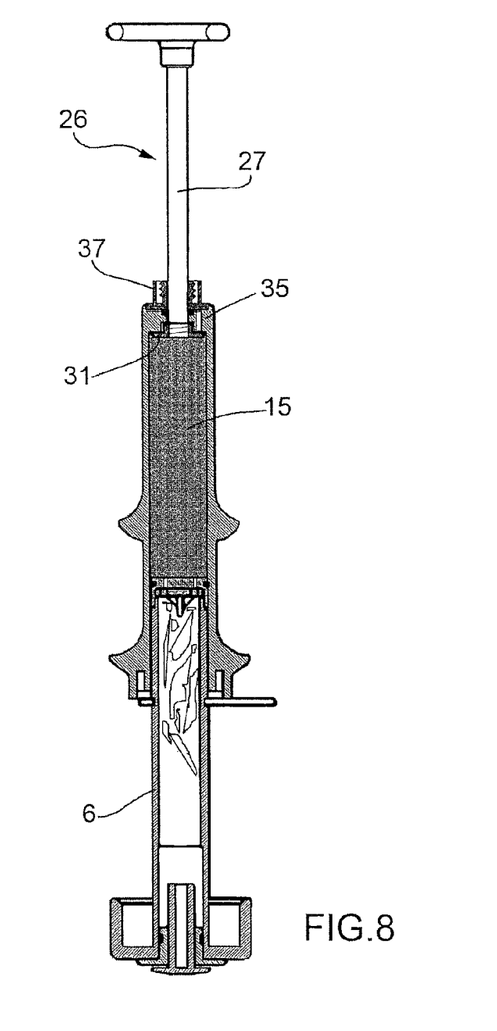
FIG. 8 is a section view of the device in yet another step of the preparation of the mixture.
Figure 9:
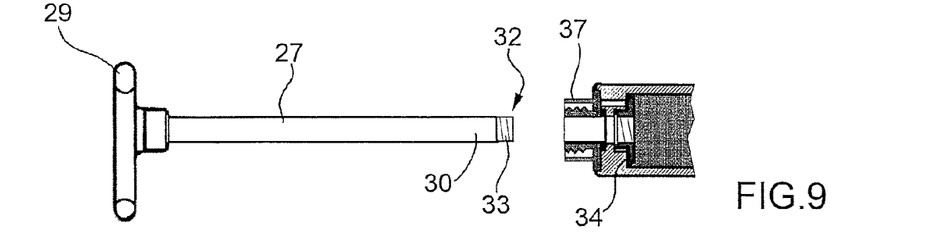
FIG. 9 is a detailed section view of the device in a final step of the preparation of the mixture.

In the tubular body 2 there is also an opening 14 for dispensing the mixture, indicated with 15 in FIG. 7 and thereafter; such a dispensing opening 14 is suitable for placing the second chamber 12 selectively in communication with the outside, and is opposite the mouth 3 in which the piston 6 is inserted.

The first chamber 10 and the second chamber 12 of the device communicate with each other through small substantially axial holes 16 foreseen in the head 7 of the piston 6.

The liquid component 11, which is volatile and toxic if released into the atmosphere, is enclosed in a hermetically closed container 17: such a container 17 consists, for example, of a glass vial. The container 17 can, nevertheless, be of another shape or another material, suitable for safely enclosing said liquid component 11. The container 17 is housed in the first chamber 10 defined in the piston 6, as can be seen in FIG. 4.

The device also comprises means for opening the container 17 of the liquid component 11, wholly indicated with 18. Such means 18 for opening the container 17 comprise a fracturing member 19, associated with the handle 9 for actuating the piston 6, selectively mobile from an outer position—represented in FIG. 5—to an inner position—represented in FIG. 6—pressing on a first end of the container 17, to cause it to break. In greater detail, the fracturing member 19 is suitable for acting upon the head of the glass vial 17. The fracturing member 19 consists of a hollow tubular portion equipped with a widening 20 at its outer end, on which it is possible to press manually; the fracturing member 19 is engaged so as to be able to slide in a bushing 21 that closes a gap 22 for access to the first chamber 10, made in the handle 9 of the piston 6, with interposition of a second sealing gasket 23.

The means 18 for opening the container 17 also comprise a protrusion 24, opposite the fracturing member 19 inside the first chamber 10, on which the second end of the container 17, i.e. the base of the glass vial, abuts. The protrusion 24 is fixedly connected to the inner face of the head 7 of the piston 6.

The first chamber 10, foreseen inside the piston 6, is equipped with a filter 25 for holding back the fragments of the container 17 after it has been broken. Indeed, such fragments, especially the smallest ones, could pass through the holes 16 and mix together, inside the second chamber 12, with the liquid component and with the powdered component. The filter 25 is positioned at the inner face of the head 7 of the piston 6, adjacent to the protrusion 24.

The device 1 comprises a mixing member 26, associated with the second chamber 12, suitable for the preparation of the mixture, i.e. suitable for making it quicker and easier to mix the liquid component and the powdered component.

More specifically, the aforementioned mixing member 26 comprises actuation means 27, for example a through stem able to slide through the dispensing opening 14, suitable for forming the mixture foreseen in the second chamber 12.

The actuation means 27 have an outer end 28 equipped with a handle 29 for manual actuation, and an inner end 30 provided with the mixing member 26, for example a mixing blade 31, which carries out the mixing of the liquid component with the powdered component.

The mixing member 26, for example the mixing blade 31, is associated with the inner end of the actuation means, for example the stem 27, through releasable connection means 32 that allow the actuation means to be separated from the mixing member 26.

This provision, as will become clearer hereafter, allows the actuation means of the mixing member 26 to be removed at the end of the preparation of the mixture, thus freeing the dispensing opening 14.

According to another version of the present invention, the releasable connection means 32 comprise a threaded portion 33 foreseen in the inner end 30 of the stem 27, and a nut screw 34 foreseen in the mixing blade 31.

According to an alternative that is not illustrated, the nut screw is located on the stem 27 and the threaded portion in the mixing member 26.

Inside the second chamber 12 the device 1 comprises a constraining element 35 for the mixing blade 31.

If the separation of the mixing member 26 from the stem 27 takes place by rotation, the constraining element 35 is made as an anti-rotation element: for example a shape connection for suitable portions of the mixing member 26, a pin, etc.

The constraining element 35 thus allows the stem 27 to be quickly removed from the blade 31 at the end of the preparation of the mixture.

According to a version of the present invention, the constraining element 35 comprises an axial pin arranged eccentrically with respect to the dispensing opening 14 of the mixture.

On the mixing member 26, or on the blade 31, near to the dispensing opening 14, there is also a recess 36 (FIG. 6), or else a hole, etc., in which a corresponding portion of the blade 31 is intended to engage at the end of the preparation of the mixture, so as to make the constraining element 35 engage in the blade 31 itself.

According to another version of the present invention, the recess 36 is prism-shaped and the blade 31 has a portion with a corresponding shape, and in this case the pin is not present, because the necessary anti-rotation constraining function is already achieved in this way.

The tubular body 2, at the dispensing opening 14 of the mixture, comprises an appendix 37 for coupling with a further recipient for collecting the dispensed mixture, not represented in the figures but of the type essentially known. The appendix 37 can be made in a separate piece from the tubular body 2, mounted with interposition of a third sealing gasket 38. Such a coupling appendix 37 comprises screw connection means to the recipient, wholly indicated with 39; the aforementioned screw connection means 39 can be of the type known in the field by the trade name "Luer—Lock™", or other equivalent means.

It should be noted that screw connection means 39 of this type are particularly recommended since, given the high density and viscosity of the prepared mixture, it is necessary to achieve secure and effective locking of the recipient, which with other less secure connection means could detach precisely due to the pressure of the mixture, compressed by the piston 6.

Figure 5:
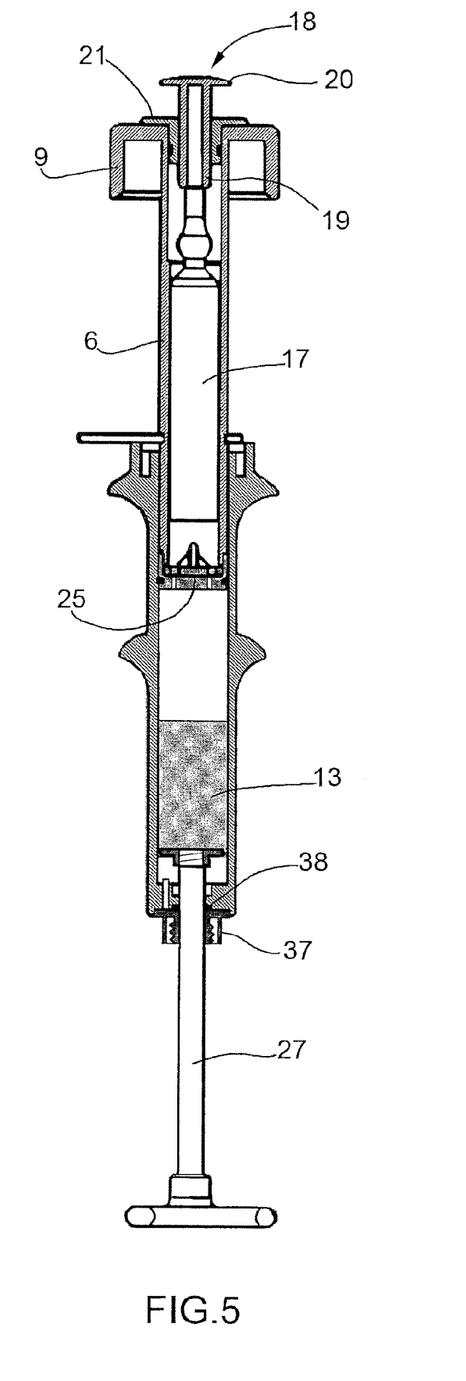
FIG. 5 is a section view of the device in an initial step of the preparation of the mixture.
Figure 6:
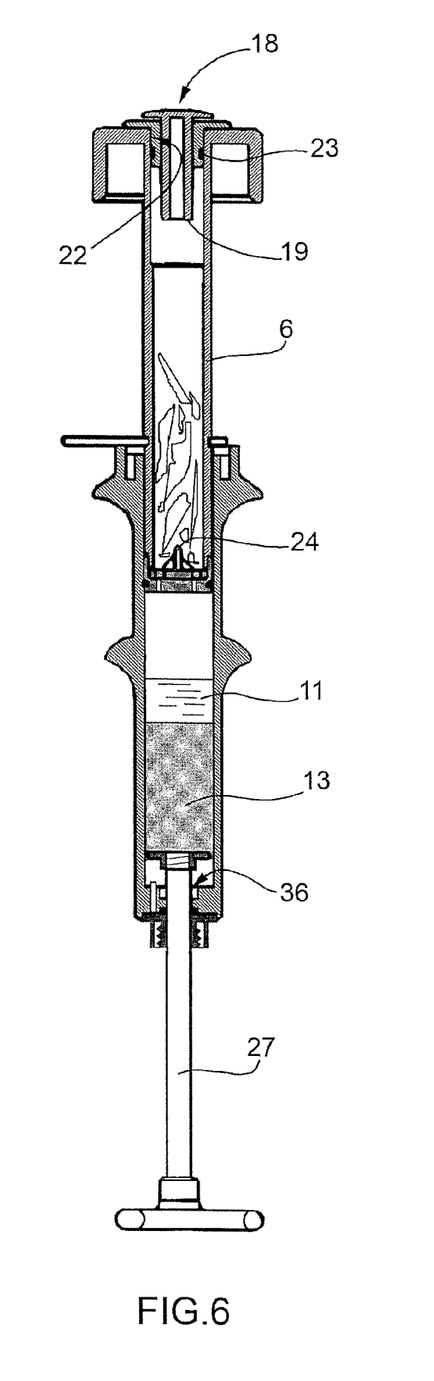
FIG. 6 is a section view of the device in a subsequent step of the preparation of the mixture.

In practical use, the device ready for use is in a condition like the one represented in FIG. 5. The preparation of the mixture for subsequent administration begins by breaking the container 17 of the liquid component 11, as can be seen in FIG. 6. In order to break the container 17, the operator presses manually, preferably with a fast and sharp gesture, on the widening 20 of the fracturing member 19. Such pressing, combined with the opposite abutment of the container on the protrusion 24, causes the container 17 itself to shatter.

At this point the liquid component 11 is freed inside the first chamber 10; through manual traction towards the outside of the piston 6 by the operator, a depression is created inside the second chamber 12. Then the liquid component 11 is drawn by the depression and transferred into the second chamber itself 12 through the holes 16.

It is now possible to mix the two components to obtain the product to be administered.

The operator therefore acts upon the mixing member 26 performing a quick alternative rotary and translation movement of the member 26 itself inside the second chamber 12.

After having obtained optimal mixing of the two components 11, 13, the operator removes the stem 27 of the mixing member 26. In particular, the operator pulls the mixing member 26 outwards until the blade 31 is engaged in the recess 36, and therefore in the anti-rotation constraining element 35. At this point, the operator can completely unscrew the stem 27 from the blade 31, removing it and thus freeing the dispensing opening 14. Advantageously, the operator can now connect the appendix 37 to a recipient for collecting the dispensed mixture, which will then be used in the surgical intervention once filled by acting manually on the handle 9 of the piston 6.

With this solution, important technical advantages are evidently obtained.

A first important technical advantage consists of the fact that, once the step of preparing the mixture inside the second chamber 12 has ended during surgery, the operator can proceed, immediately and with simple gestures, to dispense the aforementioned mixture for example inside a collection recipient.

A further technical advantage consists of the fact that the risks of contamination of the prepared mixture and also the risks of dispersion of the mixture itself in the environment are substantially reduced.

Yet another technical advantage consists of the fact that the step of preparing the mixture is particularly quick and easy thanks to the positioning of the mixing member 26 at the dispensing opening 14, also considering the high density and viscosity of the mixture itself that generate substantial resistance to the movement of the mixing member 26.

Yet another technical advantage achieved by the device according to the invention consists of the fact that the two liquid and powdered components 11, 13 are kept in areas hermetically separated from one another and with respect to the outside until the moment of actual preparation of the mixture.

Figure 10:
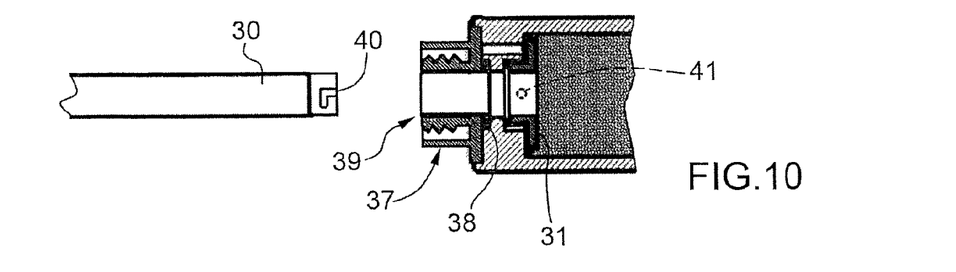
FIG. 10 is a detailed section view of another embodiment of the device.

Another embodiment of the device according to the invention is represented in FIG. 10. In this embodiment, the releasable connection means 32 comprise a bayonet coupling. For example, the inner end 30 of the stem 27 comprises one or more grooves 40, whereas the blade comprises one or more ridges 41 suitable for engaging in the groove 40. This embodiment allows the stem 27 to be released from the blade 31 more quickly; however, this solution is recommended for devices suitable for preparing small amounts of mixture, since the bayonet coupling makes a less solid coupling with respect to one with screw means.

Figure 11:
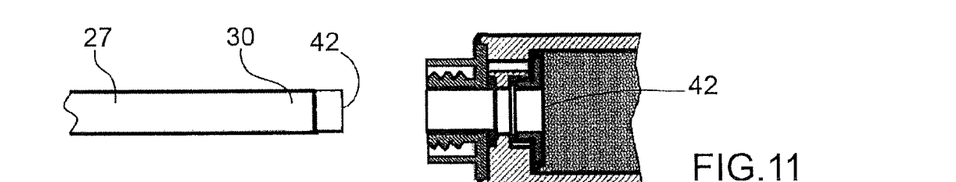
FIG. 11 is a detailed section view of yet another embodiment of the device.
Figures 11A, 12:
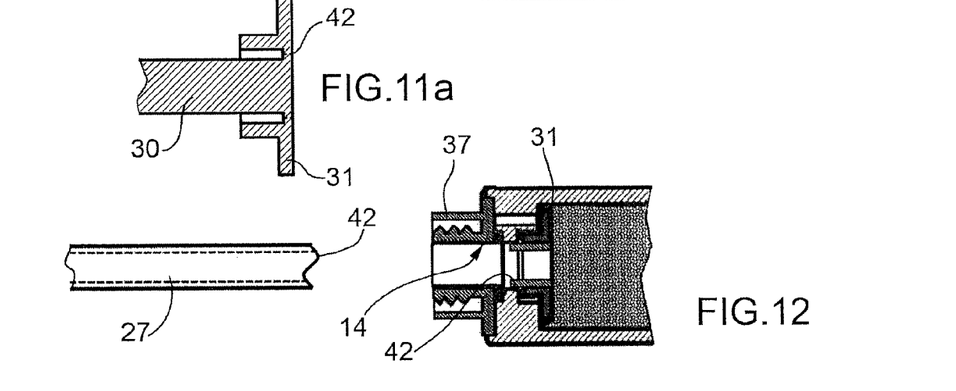
FIG. 11a is a detail of FIG. 11.
FIG. 12 is a detailed section view of yet another embodiment of the device.

Another embodiment of the device according to the invention is represented in FIGS. 11, 11a. In this embodiment the releasable connection means 32 comprise a traction breaking portion 42 of the stem 27. For example, such a breaking portion 42 can consist of a sort of thin membrane configured like the inner face of the blade 31, which fractures perimetrically by traction of the stem 27 and that frees the dispensing opening 14, as can be seen in FIG. 11a.

Also in this embodiment the removal of the stem can take place extremely quickly.

Another embodiment of the device according to the invention is represented in FIG. 12. In this embodiment, the stem 27 is made internally hollow and the releasable connection means 32 comprise a breaking portion 42 foreseen along the side surface of the stem 27 itself. By manual traction, the latter fractures into two pieces the inner one of which stays fixedly connected to the blade 31, and therefore constitutes a channel for dispensing the mixture.

Figure 13:
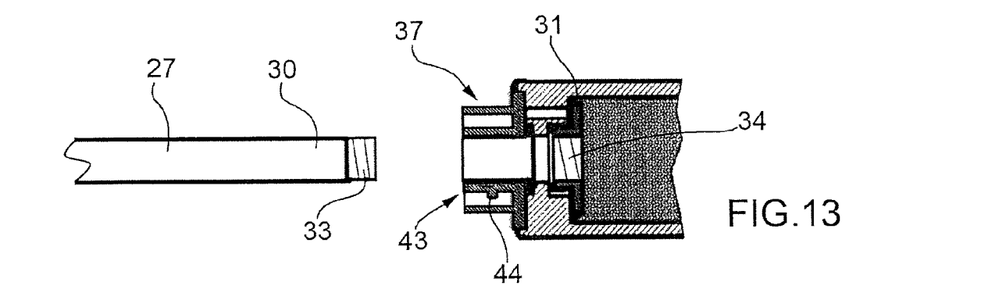
FIG. 13 is a detailed section view of a further embodiment of the device according to the invention.

Another embodiment of the device according to the invention is represented in 10 FIG. 13. In this embodiment the coupling appendix 37 comprises bayonet coupling means 43 with the recipient for collecting the dispensed mixture. In particular, the appendix 37 comprises at least one ridge 44 suitable for engaging in a respective groove foreseen in the mouth of the recipient, not represented in. the figure but of the conventional type. This solution makes it 15 possible to make the connection of the device to the collection recipient even quicker and simpler.

If the device is relatively large in size, to thus produce relatively large amounts of mixture, the dispensing opening 14 must also be larger. In this case, so as to still keep the diameter of the stem 27 small, it is possible to foresee a reducer bushing, or other equivalent means, to be removed together with the stem itself 27.

It has thus been seen how the invention achieves the proposed purposes. The present invention has been described according to preferred embodiments, but equivalent variants can be conceived without departing from the scope of protection offered by the following claims.

The invention claimed is:

1. A device to prepare and administer a two-component mixture, comprising a first chamber in which a container is housed that is hermetically closed for a liquid component, a second chamber, containing a powdered component, communicating with said first chamber, means for opening said container of the liquid component, a mixing member associated with said second chamber for preparing the mixture and a piston able to move in said second chamber to dispense the mixture, wherein said mixing member comprises actuation means for actuating the mixing member itself, said actuation means being able to be actuated from outside of the device, said actuation means and said mixing member being associated through releasable connection means, said actuation means for actuating comprising a stem sliding through a dispensing opening foreseen in said second chamber, said dispensing opening being suitable for dispensing the mixture and for placing said second chamber in communication with the outside, said dispensing opening being opposite to a mouth of said second chamber in which said piston is inserted, further comprising a tubular body that defines said second chamber, wherein said tubular body, at said opening for dispensing the mixture, comprises an appendix for coupling with a further recipient, and wherein said appendix for coupling comprises a screw connection means to said recipient.

2. The device according to claim 1, wherein said actuation means comprises an outer end equipped with a handle.

3. The device according to claim 1, wherein said actuation means comprises an inner end associated with said mixing member.

4. The device according to claim 1, wherein said mixing member comprises a mixing blade.

5. The device according to claim 1, wherein said releasable connection means comprises a breaking portion of said actuation means.

6. A device to prepare and administer a two-component mixture, comprising a first chamber in which a container is housed that is hermetically closed for a liquid component, a second chamber, containing a powdered component, communicating with said first chamber, means for opening said container of the liquid component, a mixing member associated with said second chamber for preparing the mixture and a piston able to move in said second chamber to dispense the mixture, wherein said mixing member comprises actuation means for actuating the mixing member itself, said actuation means being able to be actuated from outside of the device, said actuation means and said mixing member being associated through releasable connection means, said actuation means for actuating comprising a stem sliding through a dispensing opening foreseen in said second chamber, said dispensing opening being suitable for placing said second chamber in communication with the outside, said dispensing opening being opposite to a mouth of said second chamber in which said piston is inserted, wherein said releasable connection means comprises a separable coupling means and wherein said separable coupling means comprises a matching shape coupling means.

7. The device according to claim 6, wherein said matching coupling means comprises a threaded portion in an inner end of the actuation means, and a nut screw in said mixing member, or a nut screw in said inner end of the actuation means, and a threaded portion in the mixing member.

8. The device according to claim 1, wherein said releasable connection means comprises a bayonet type coupling.

9. The device according to claim 1, A device to prepare and administer a two-component mixture, comprising a first chamber in which a container is housed that is hermetically closed for a liquid component, a second chamber, containing a powdered component, communicating with said first chamber, means for opening said container of the liquid component, a mixing member associated with said second chamber for preparing the mixture and a piston able to move in said second chamber to dispense the mixture, wherein said mixing member comprises actuation means for actuating the mixing member itself, said actuation means being able to be actuated from outside of the device, said actuation means and said mixing member being associated through releasable connection means, said actuation means for actuating comprising a stem sliding through a dispensing opening foreseen in said second chamber, said dispensing opening being suitable for placing said second chamber in communication with the outside, said dispensing opening being opposite to the mouth of said second chamber in which said piston is inserted, wherein said actuation means for actuating the mixing member comprises an internally hollow stem and said releasable connection means comprises a breaking portion along a side surface of said stem.

10. A device to prepare and administer a two-component mixture, comprising a first chamber in which a container is housed that is hermetically closed for a liquid component, a second chamber, containing a powdered component communicating with said first chamber means for opening said container of the liquid component, a mixing member associated with said second chamber for preparing the mixture and a piston able to move in said second chamber to dispense the mixture, wherein said mixing member comprises means for actuating the mixing member itself, said actuation means being able to be actuated from outside of the device, said actuation means and said mixing member being associated through releasable connection means, said means for actuating comprising a stem sliding through a dispensing opening foreseen in said second chamber, said dispensing opening being suitable for placing said second chamber in communication with the outside, said dispensing opening being opposite to the mouth of said second chamber in which said piston is inserted, further comprising a constrainment element for said mixing member inside said second chamber, said constraining element promoting a separation of the mixing member of the actuation means.

11. The device according to claim 10, wherein constraining element is made as an anti-rotation element for said mixing member.

12. The device according to claim 1, wherein said hermetically closed container for the liquid component consists of a glass vial.

13. The device according to claim 1, wherein said first chamber for the liquid component is inside said piston for dispensing the mixture.

14. The device according to claim 1, wherein said means for opening said container comprises a fracturing member, associated with the handle for actuating said piston, selectively mobile from an outer position to an inner position pressing on a first end of said container to cause the container to break.

15. The device according to claim 1, wherein said means for opening said container comprises a projection, opposite said fracturing member inside said first chamber, on which a second end of said container abuts.

16. The device according to claim 1, wherein said piston for dispensing the mixture comprises a head equipped with at least one hole for passage of the liquid component from said first chamber to said second chamber.

17. The device according to claim 1, wherein said first chamber is equipped with a filter for holding back fragments of said container of the liquid component after the container is broken.

18. The device according to claim 1, further comprising a wherein the tubular body that defines said second chamber comprises a mouth in which said piston engages, defining said first chamber.

19. The device according to claim 1, wherein said appendix for coupling with a further recipient is for collecting the dispensed mixture.

20. The device according to claim 1, wherein said appendix for coupling comprises a bayonet coupling means with said recipient.

21. The device according to claim 1, wherein said piston is able to slide axially inside said second chamber.

22. The device according to claim 1, wherein said piston is associated with said second chamber through a screw-nut screw coupling.

* * * * *